United States Patent
Singh et al.

(10) Patent No.: US 8,152,980 B2
(45) Date of Patent: Apr. 10, 2012

(54) ELECTRONICALLY CONDUCTING CERAMIC ELECTRON CONDUCTOR MATERIAL AND THE PROCESS FOR PRODUCING AN AIR-TIGHT SEAL IN AN OXYGEN SENSOR WITH AN INTERNAL REFERENCE

(75) Inventors: Dileep Singh, Naperville, IL (US); Jules Routbort, Hinsdale, IL (US); Prabir Dutta, Worthington, OH (US); John V. Spirig, Somerset, NJ (US)

(73) Assignee: UChicago Argonne, LLC, Chicago, IL (US)

( * ) Notice: Subject to any disclaimer, the term of this patent is extended or adjusted under 35 U.S.C. 154(b) by 123 days.

(21) Appl. No.: 11/861,941

(22) Filed: Sep. 26, 2007

(65) Prior Publication Data

US 2009/0078025 A1    Mar. 26, 2009

(51) Int. Cl.
*G01N 27/409* (2006.01)
*G01N 27/403* (2006.01)

(52) U.S. Cl. ........ 204/427; 204/424; 204/431; 205/782; 205/784; 205/784.5

(58) Field of Classification Search ............... 73/31.04; 204/400–435; 205/775–794.5
See application file for complete search history.

(56) References Cited

U.S. PATENT DOCUMENTS

| | | | | |
|---|---|---|---|---|
| 5,827,415 A | * | 10/1998 | Gur et al. | 204/426 |
| 6,974,070 B2 | | 12/2005 | Goretta et al. | |
| 2003/0027033 A1 | | 2/2003 | Seabaugh et al. | |
| 2003/0121801 A1 | * | 7/2003 | Inaba et al. | 205/785.5 |
| 2006/0213771 A1 | | 9/2006 | Routbort et al. | |
| 2007/0037031 A1 | | 2/2007 | Cassidy et al. | |

FOREIGN PATENT DOCUMENTS

JP     05009057 A    *   1/1993

OTHER PUBLICATIONS

Q X Fu, F. Tietz, P. Lersch, D. Stover "Evaluation of Sr- and Mn-substituted LaAlO3 as potential SOFC anode materials" Solid State Ionics 177 (2006), 1059-1069.*
machine translation of JP05-009057A, Aizawa et al. Jan. 1993.*
Spirig et al., "Joining of Highly Aluminum-Doped Lanthanum Strontium Manganese Oxide with Tetragonal Zirconia by Plastic Deformation", Solid State Ionics, 179 (2008) pp. 550-557.

* cited by examiner

*Primary Examiner* — Kaj K Olsen
*Assistant Examiner* — Susan Thai
(74) *Attorney, Agent, or Firm* — Foley & Lardner LLP

(57) ABSTRACT

A method and an article of an electrically conductive ceramic interconnect bonded to a compatible ceramic housing for an oxygen partial pressure sensor system. The interconnect includes a $La_xSr_yAl_zMn_{1-z}O_3$ (LSAM) having a stoichiometry enabling good electrical conductivity at high temperatures and the LSAM also bonded to a yttria stabilized zirconia forming a stable and durable seal.

8 Claims, 8 Drawing Sheets

ELECTRONICALLY CONDUCTING CERAMIC ELECTRON CONDUCTOR MATERIAL AND THE PROCESS FOR PRODUCING AN AIR-TIGHT SEAL IN AN OXYGEN SENSOR WITH AN INTERNAL REFERENCE

The United States Government has certain rights in this invention pursuant to Contract No. W-31-109-Eng-38 between the Unites States Government and the University of Chicago and/or pursuant to Contract Nos. DE-ACO2-06CH11357 and DE-PS26-02NT41422 between the United States Government and UChicago Argonne, LLC representing Argonne National Laboratory and grant DE-FC 26 03NT41615 to Ohio State University.

This invention is directed to a conducting ceramic material for use as an electron carrier for signal measurement in an oxygen sensor system. More particularly the invention is directed to a lanthanum/strontium/aluminum/manganese/oxide (LSAM) compound for use as an electron conductor for an oxygen sensor system, the aluminum-doped lanthanum strontium manganese oxide perovskite compound which enables reliable oxygen partial pressure measurements at high temperatures and also enables a highly stable, gas-tight mechanical seal between the ceramic electrode and a system housing.

BACKGROUND OF THE INVENTION

Numerous industrial systems involve operation at high temperatures in which an important operating parameter is the oxygen partial pressure. Consequently, it is imperative to monitor and control the oxygen partial pressure associated with the thermodynamic environment and operating conditions of the particular industrial process. Due to the harsh operating environment, many oxygen sensors cannot even be placed in the most useful monitoring location, resulting in reduced accuracy and response time for such an inferential monitoring system. Some systems have been developed to be operative at high temperatures and harsh chemical environments, such as is described in a US patent application having publication number U 2006/0213771 A1, a filing of the instant title holder; and this application is incorporated by reference herein in its entirety. However, this system uses platinum electrodes for measuring the current arising from the oxygen partial pressure difference between the pressure derived from decomposition of a metal/metal oxide powder disposed inside a sealed yttrium-stabilized tetragonal zirconia polycrystal (YTZP) cylinder or housing and an external oxygen environment. It has proven difficult to produce a gas-tight seal between the Pt electrode and the YTZP. Hence, glass is used to seal the Pt electrode to the housing, and glass seals are notoriously lacking in durability and reliability.

SUMMARY OF THE INVENTION

These significant problems of conventional oxygen partial pressure measurement systems are overcome by using electrically conducting ceramic interconnects of $La_xSr_yAl_z Mn_{1-z}O_3$ that allows for A-site deficiency (hereinafter, LSAM) with the aluminum addition to $La_xSr_yMnO_3$ (LSM) stabilizing the material in potential reactions with a sensor housing of yttrium stabilized zirconia (YTZP) and also providing a compatible thermal expansion coefficient between LSAM and YTZP. Other suitable materials include $CeO_2$, brownmilleritory rare earth perovskites, only any such ceramic materials whose oxygen ion conductivity is at least ten times greater than its electrical conductivity.

The Pt electrode is embedded in the LSAM and forms intimate electrical contact with it; but it is the LSAM interconnect, not the Pt, that forms the gas-tight seal with the housing containing the metal/metal oxide internal reference. The LSAM can be conveniently used in the form of solid pieces or tape. The LSAM conductor is joined to the YTZP by plastic deformation at temperatures between about 1250°-1350° C. at stresses of approximately 10-50 MPa using strain rates ranging between about 5 to $50 \times 10^{-6}$/sec. This results in a chemically and thermally stable joint with reliable electrical conductivity at high temperatures and forms a gas-tight durable seal to the system housing.

These and other objects, advantages and features of the invention, together with the organization and manner of operation thereof, will become apparent from the following detailed description when taken in conjunction with the accompanying drawings.

DETAILED DESCRIPTION OF THE PREFERRED EMBODIMENTS

Figure 1:
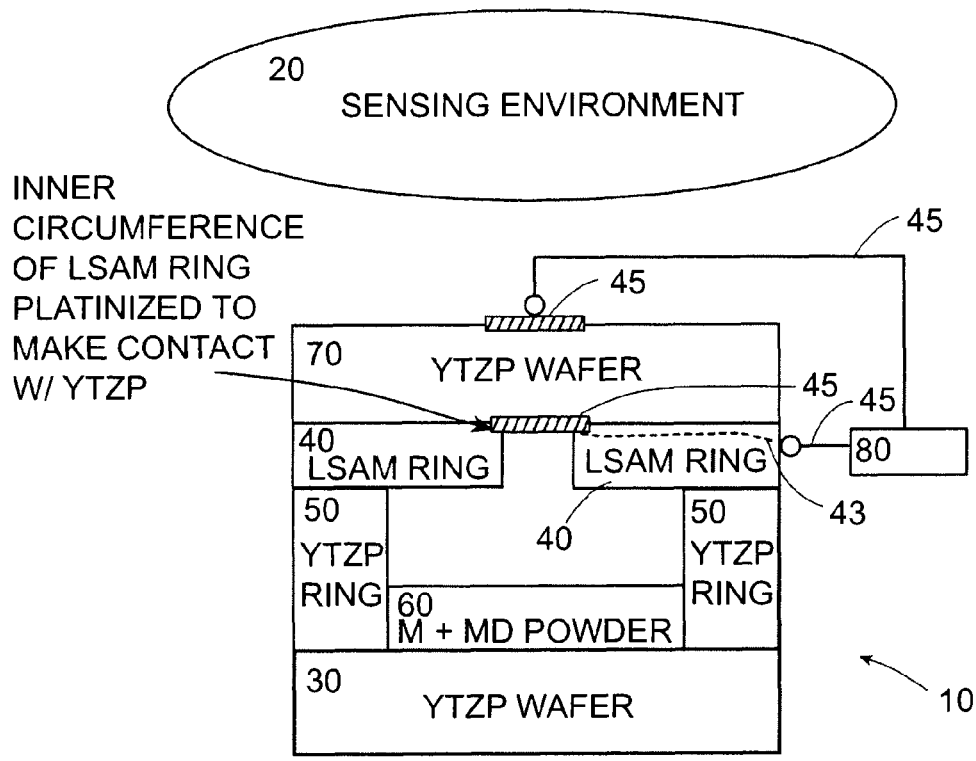
FIG. 1 illustrates a high-temperature potentiometric oxygen sensor with an internal reference and with an LSAM electrically conductive interconnect.

An oxygen sensor 10 constructed in accordance with a preferred embodiment is shown in FIG. 1. The oxygen system 10 is disposed in an industrial environment 20 in order to monitor and/or control oxygen partial pressure. The industrial environment 20 can, for example, include an internal combustion engine in any type of machine, a high-temperature fuel cell, an environmental pollution control system and a chemical processing line or stand alone system. As shown in FIG. 1, the oxygen sensor system 10 includes a YTZP base 30, an LSAM conductor 40 bonded to a YTZP ring 50; and the YTZP ring 50 is also bonded to the YTZP base 30. The bonding can be accomplished by a high-temperature bonding process described hereinafter. The oxygen sensor system 10 further includes a conventional internal reference material 60, such as a metal and metal oxide powder, and also includes a YTZP electrolyte 70. This oxygen sensor system 10 functions to measure the partial oxygen pressure in the industrial environment 20, outputting a sensor current through the LSAM electron conductor 40 (see example electron flow path 43 in the LSAM conductor 40) to a Pt electrode 45 at an inner circumference of the LSAM conductor 40 and at the edge of the sensor system 10. As shown in FIG. 1, the Pt electrode 45 is also coupled from the LSAM 40 and further disposed on top of the system 10, affixed to electrolyte 70 in order to carry out detection and processing by conventional electronics 80. The LSAM conductor 40 is interposed between the various YTZP elements 30 and 50 in an internal reference potentiometric oxygen sensor. As the LSAM 40 undergoes grain boundary sliding in the same temperature and load regime as the YTZP 30, 50, a gas-tight and pore free joint can be created between these elements. This enables the creation of a high temperature oxygen sensor system 10 in a single high pressure/high temperature processing step. The quality of the joint between these two material types precludes the use of secondary sealing agents such as brazes or glass. As the LSAM 40 exhibits a lower resistivity than the YTZP 30, 50, it serves as the medium by which current is pulled from the internal Pt electrode 45 to measure the voltage of the internal reference oxygen sensor. The LSAM 40 outputs a voltage signal from the system 10 with the voltage signal determined by a Nernst relationship characteristic of the oxygen partial pressure and the industrial environment 20 and that of the internal reference as calculated from an Ellingham diagram.

Figure 2:
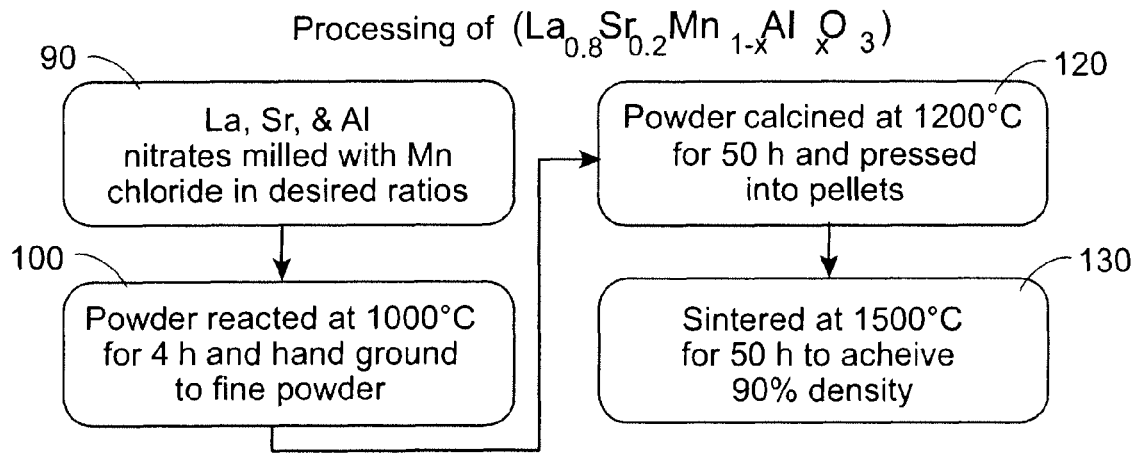
FIG. 2 illustrates one example of manufacture of $(La_{0.8}Sr_{0.2})Mn_{1-x}Al_xO_3$.

Preparation of the LSAM conductor 40 is readily accomplished by any one of a variety of conventional processes for preparing ceramics. In a preferred method shown in FIG. 2, La, Sr, and Al nitrates are milled to a coarse powder with Mn chloride in step 90 in preselected weight ratios to achieve a desired end composition. In step 100 powders are reacted at about 1000° F. for four (4) hours, and reacted powders are ground to a fine powder material. In step 120 this fine powder is calcined at 1200° C. for 50 h and ground into powder and pressed into pellets which can then be further densified or cast into a green tape. In step 130 these pellets are rendered at 1500° C. for 50 h to achieve about a 90% density. The resulting product can then be used to form into a desired shape and size to be integrated as the LSAM conductor 40 into the oxygen sensor system 10. Further details of preparation of LSAM are set forth in Example I.

In order to effectuate joining of dissimilar materials to form portions of the oxygen sensor system 10, in this case the YTZP base 30, YTZP ring 50 and the LSAM conductor 40, these components should be joined such that they can withhold thermal stresses to be encountered when operating in the oxygen sensor system 10. A preferred method to accomplish this joining is by high-temperature plastic deformation. This is shown schematically in FIG. 3 for joining LSAM wafer 150 to YTZP wafer 160. In this process, the materials are bonded together by stressing each material to the point where it deforms plastically and intersperses with the other material.

Since cubic YSZ doesn't deform at the same temperatures as the LSAM 40, the preferred material YTZP and LSAM can both deform plastically in the same temperature and stress regime through a grain-boundary-sliding (GBS) mechanism. GBS is a diffusion-controlled process and is generally achieved at approximately one half the melting temperature of the material. This joining process is fundamentally different from direct diffusion bonding. Samples joined by direct diffusional bonding do not deform plastically, requiring very smooth surfaces and very high temperatures ($0.8T_{mp}$, where $T_{mp}$ is the melting temperature (K)). Conventionally, joints created via a plastic flow process are between identical or compositionally graded materials.

In the present embodiment, a highly Al-doped polymorph of LSAM is joined to the YTZP material by plastic flow without any special preparation of the mating surfaces. After the joining operation, the microstructure of the interface was examined by electron microscopy, and Raman spectroscopic maps of the joining planes are employed to look for chemical reactions between the starting materials and the possible creation of new phases at the interlayers. In this manner, a method of bonding wholly dissimilar components for use in high-temperature environments is enabled. This highly aluminum-doped perovskite (LSAM) enables using more conducting forms of LSAM as an alternative to conventional Pt conductors in high-temperature applications, thereby solving a variety of problems described hereinbefore.

Figure 5:
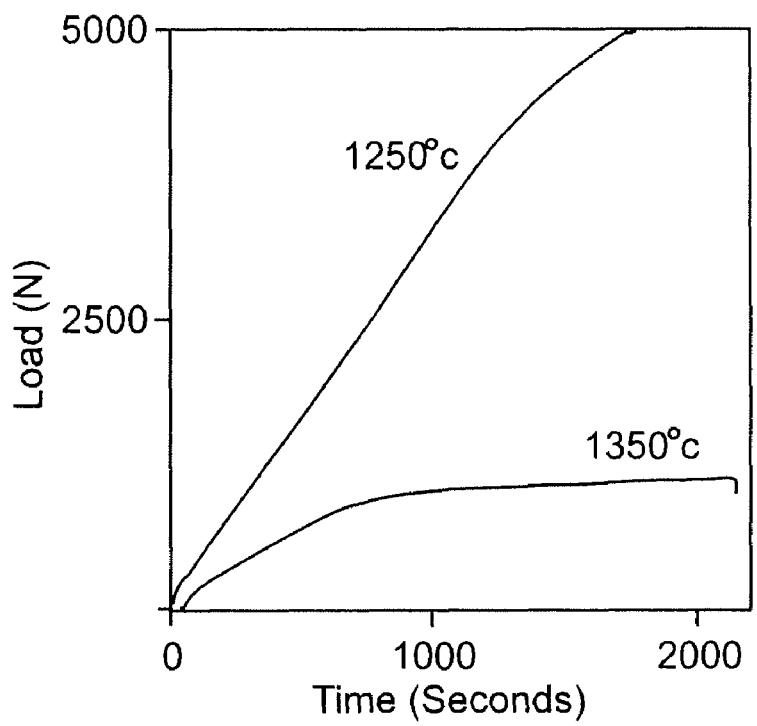
FIG. 5 illustrates load versus time for $La_{0.77}Sr_{0.20}Al_{0.1}O_3$ sandwiched between wafers at YTZP at 1250° and 1350° C.

In the basic joining process, compressive deformation of LSAM at $\dot{\epsilon}=4.5\times10^{-5}$/sec and 1250° C. resulted in a steady-state stress of ~36 MPa. The load versus time curve for the joining of YTZP to LSAM at 1250 and 1350° C. is shown in FIG. 5. The load was applied until the maximum of the load cell (5 kN) was reached or a steady state was established. At this time, the load was backed off and the amount of plastic deformation recorded. For samples joined at 1250 and 1350° C., $\Delta L/L$ ~3.5-7% were observed. L is the height of the YTZP/LSAM/YTZP sandwich prior to joining and $\Delta L$ is the length change measured after deformation and joining. At 1350° C. the stress on the sandwich was ~10 MPa. Further details of joining of YTZP and LSAM are set forth in Example II along with details shown in FIG. 3.

Figure 6A:
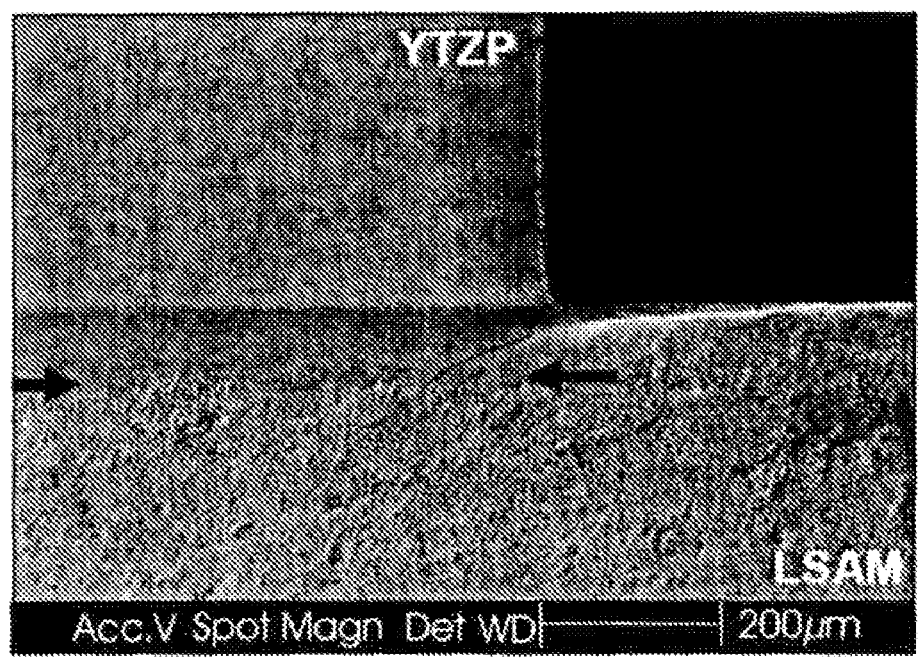
FIG. 6A is a micrograph of a joining plane of $La_{0.77}Sr_{0.20}Al_{0.9}Mn_{0.1}$, $O_3$ joined to YTZP at 1250° C. with arrows indicating the joining plane.
Figure 6B:
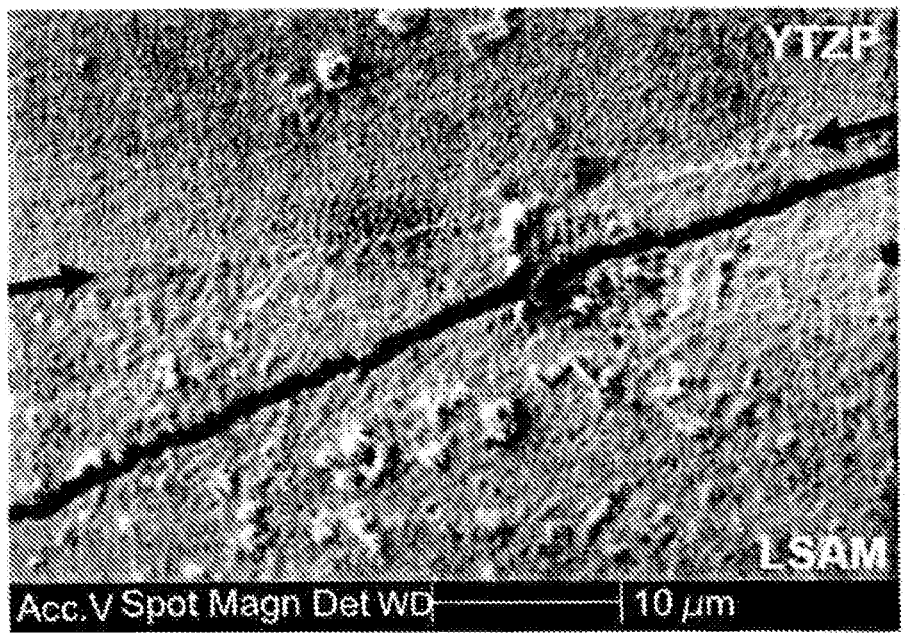
FIG. 6B shows a higher magnification micrograph of a portion of the joining plane from FIG. 6A.
Figure 7:
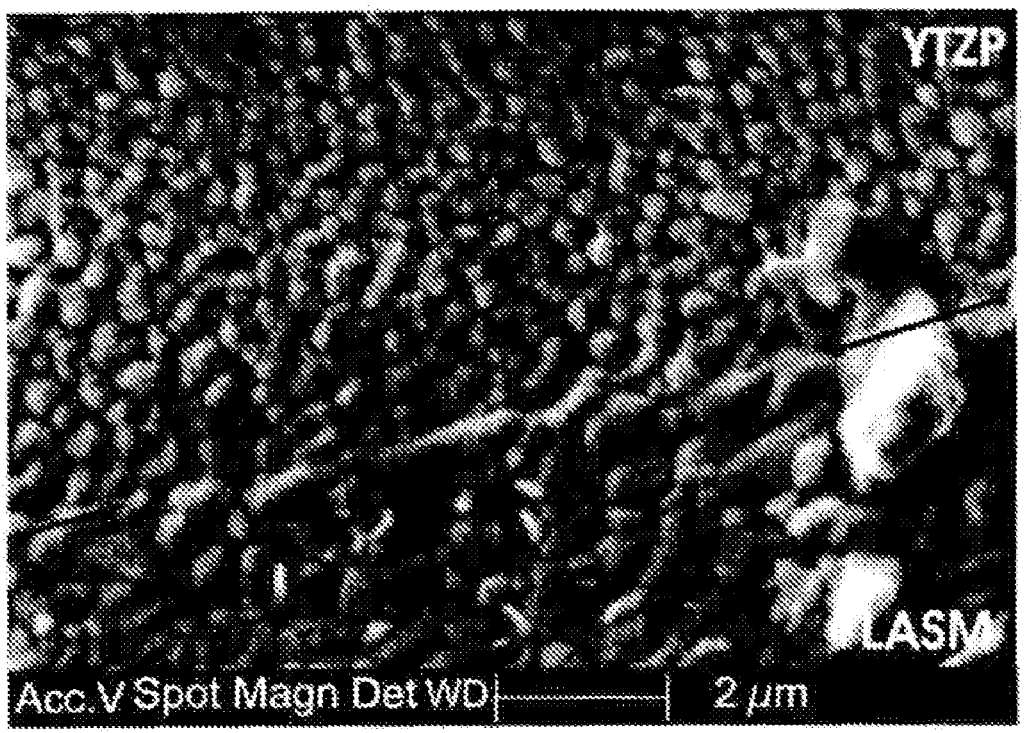
FIG. 7 illustrates a high resolution SEM image of the joining plane in YTZP/LSAM joined at 1250° C. (the arrow indicates the joining plane)

SEM micrographs of the resulting joints produced at 1250° and 1350° C. at two different magnifications are presented in FIGS. 6A/6B and 6C/6D, respectively. As there are two distinct materials, the joining planes are clearly distinguishable from the bulk ceramics (indicated by arrows in each image). The porosity of LSAM observed in FIGS. 6A/6B and 6C/6D is the result of imperfect densification. A high-resolution SEM image of the joint produced at 1250° C. is presented in FIG. 7.

Figure 6C:
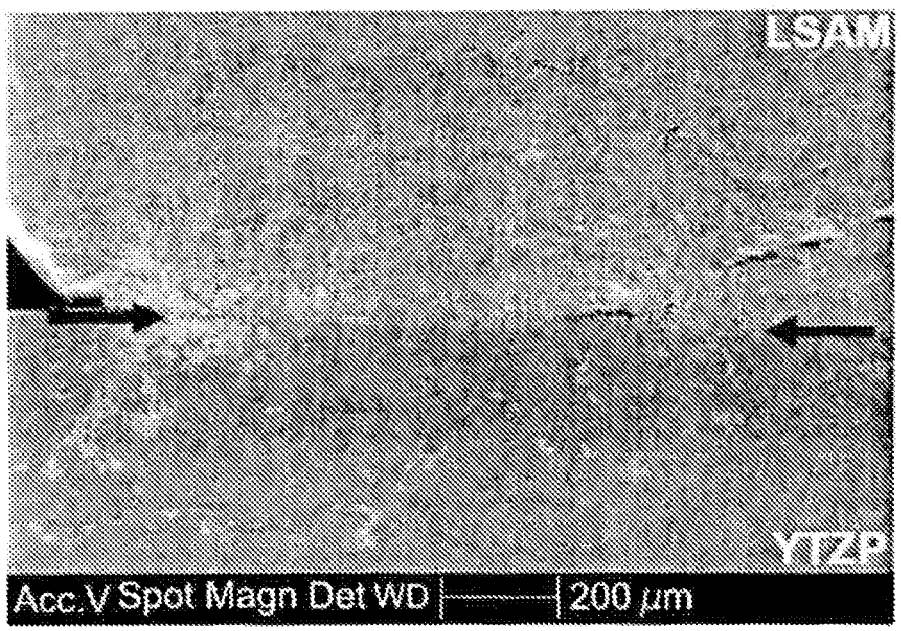
FIG. 6C shows the joining plane of the LSAM material joined to YTZP at 1350° C.
Figure 6D:
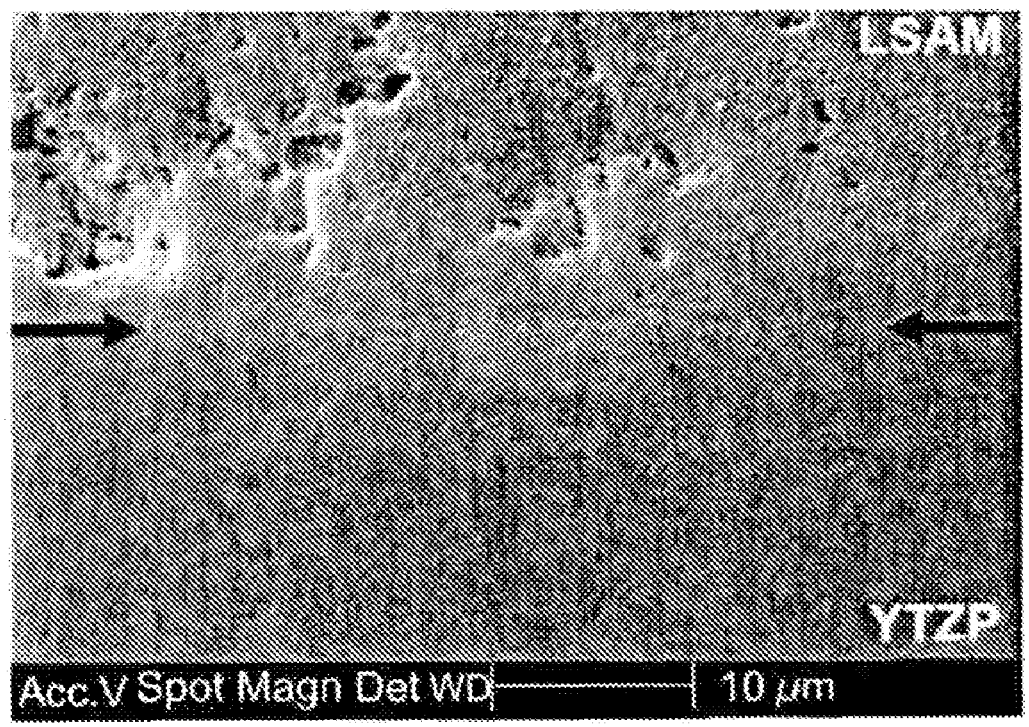
FIG. 6D is a higher magnification view of the joining plane of FIG. 6C.

LSAM wafers were not perfectly cylindrical and slightly larger than YTZP wafer. In locations where the width of the LSAM wafer exceeded that of the YTZP wafer, as exhibited in FIG. 6A, the YTZP penetrated LSAM such that the true joining plane is several microns below the point of contact prior to joining. Cracking is observed in FIG. 5A and above the joining plane in FIG. 6C. As all cracks tend to be away from the joining plane, it is believed they are artifacts of the cutting process.

Raman/spectra were taken of unjoined YTZP and LSAM wafers of as controls. The spectrum of YTZP in FIG. 8B exhibited peaks at 146, 260, 322, 402, 463, 642, 957, and 1001 $cm^{-1}$, consistent with literature. The spectrum of unjoined LSAM in FIG. 8A exhibited peaks at 567 and 745 $cm^{-1}$. As shown in FIGS. 6A-6D, the LSAM exhibited signs of porosity. The spectrum in FIG. 8A, curve B, was collected from a porous region of the LSAM control. As compared to FIG. 8A, curve A, there is a shift of the 567 cm$^{-1}$ peak to 570 cm$^{-1}$, along with a significant increase in intensity. The intensity variation is attributed to the crystallites within pores under less strain than crystallites located in fully dense regions.

Figure 8B:
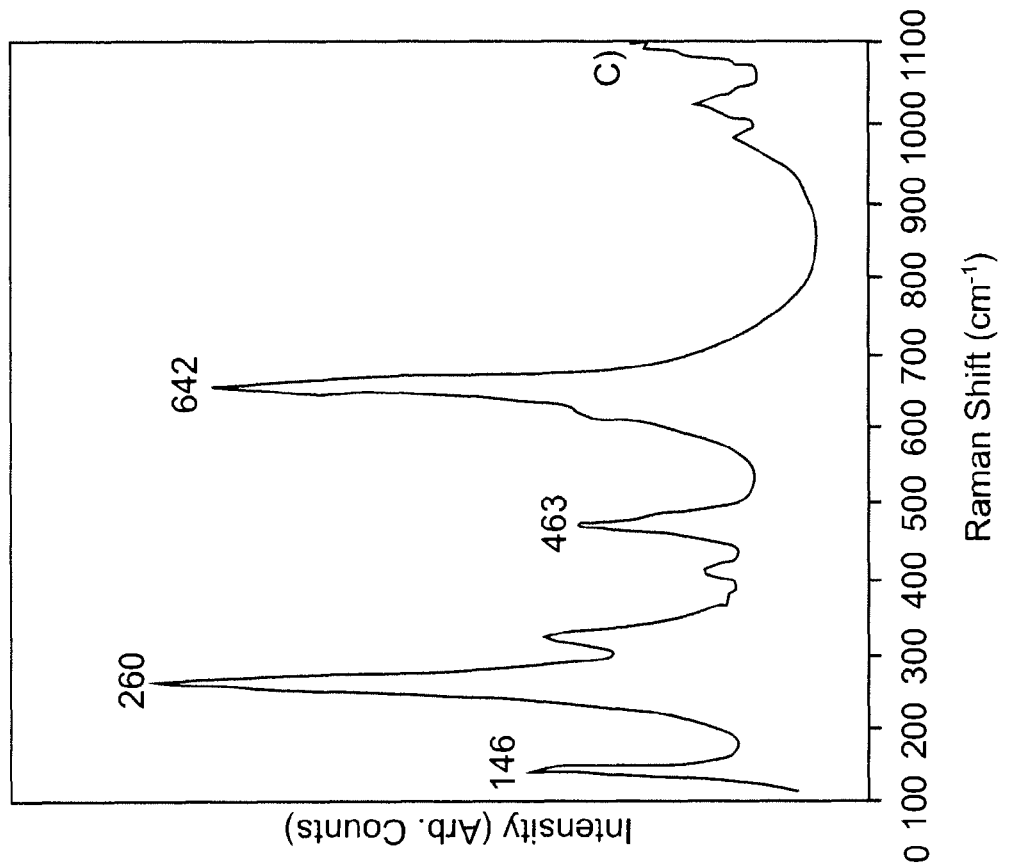
FIG. 8B shows a Raman spectrum of an unjoined wafer of YTZP.
Figure 8A:
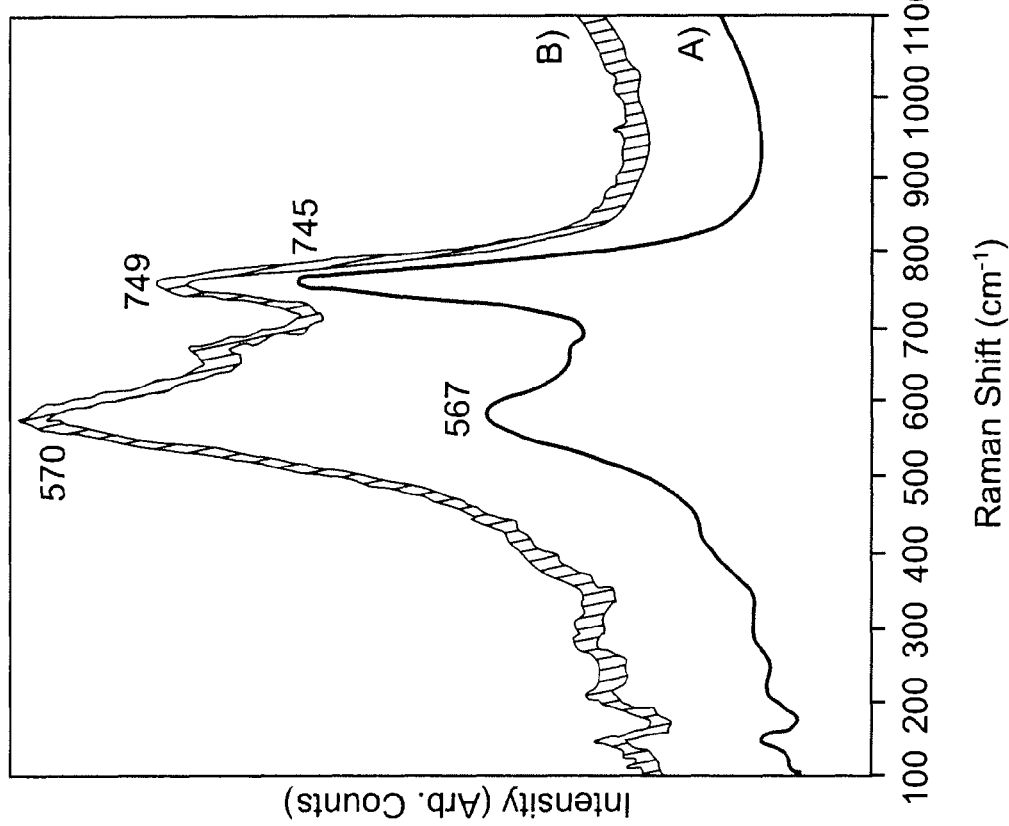
FIG. 8A shows a Raman spectrum (curve A) of an unjoined $La_{0.77}Sr_{0.20}Al_{0.9}Mn_{0.1}O_3$ pellet densified at 1500° C. and also (curve B) shows a Raman spectrum of a pore region within the densified mass of LSAM.
Figure 9A:
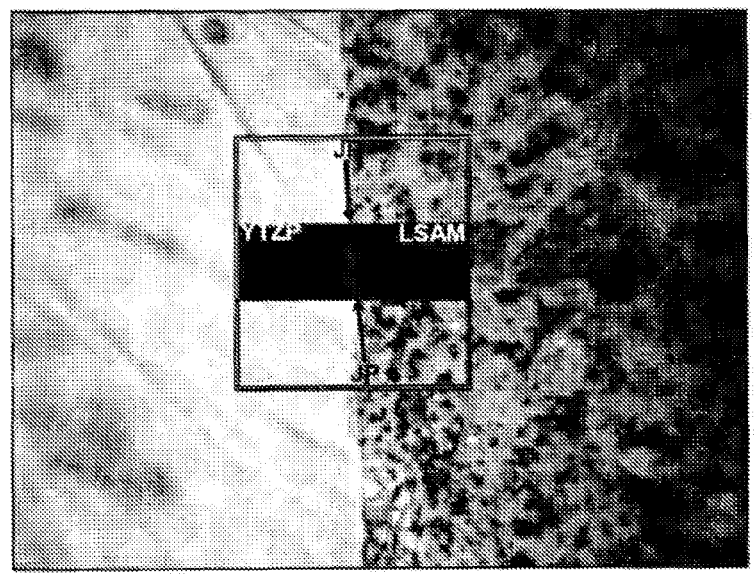
FIG. 9A illustrates a Raman image of YTZP/LSAM joined at 1250° C.
Figure 9B:
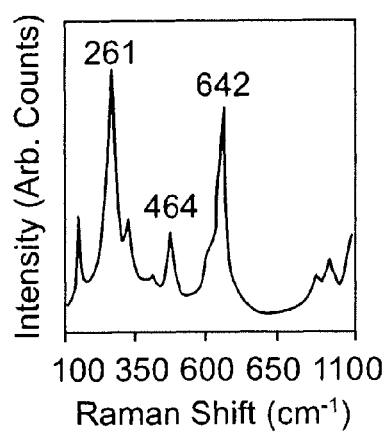
FIG. 9B shows a representative Raman spectrum of the YTZP region of FIG. 9A.
Figure 9C:
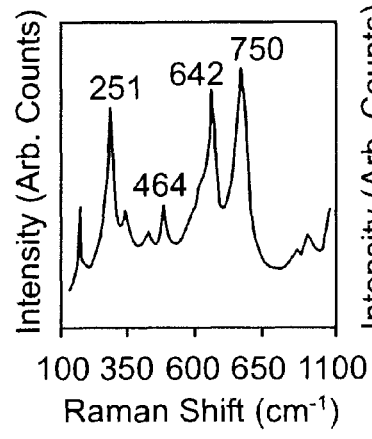
FIG. 9C shows a representative spectrum of the joining plane in FIG. 9A with the plane shown by arrows "JP"
Figure 9D:
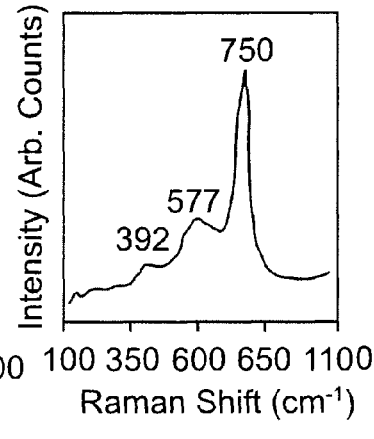
FIG. 9D shows a representative Raman spectrum of the LSAM region of FIG. 9A.

Raman maps along the joining plane between the YTZP and LSAM are presented in FIGS. 9A-9D and 10. The scanned regions are presented within the view from the 50× objective so the joining plane is clearly visible. In this manner, it is possible to determine the extent to which the LSAM phase reacted with the YTZP. The laser was line-focused to a 1×32 μm$^2$ illumination area and moved across the joining plane in 0.5 μm increments in the x-direction and 1.056 μm increments in the y-direction. In the samples joined at 1250° and 1350° C., the sizes of the scanned areas were 67×32 μm and 37×62 μm, respectively. The large area marked in FIGS. 9A-9D and 10A-10D is a ≧90% match to the YTZP control (FIG. 8B). The representative spectrum of the YTZP control region is shown in FIG. 9A. The large region on the right is a ≧90% match to the LSAM control (FIG. 8A, curve B). The representative spectrum of the LSAM control is shown in FIG. 9D. Within the bulk of the LSAM control, islands of poor comparisons are noted by dark spots due to mismatch with the control LSAM sample. These regions exhibit an intensity change of the spectral feature found at 567 cm$^{-1}$ as shown in the difference between spectra of FIG. 8A. This change in intensity accounts for the poor scoring.

The joining plane is the narrow region sandwiched between the YTZP bulk and LSAM bulk. This region is marked as "JP" and designated by the thin black area between the arrows in FIGS. 9A-9D and 10A-10D. Raman spectra from the joining plane exhibit features of YTZP and LSAM. The representative spectra from this region are shown in FIGS. 9C and 10C. No new Raman peaks indicate the absence of any new phases in the joining plane.

Figure 10A:
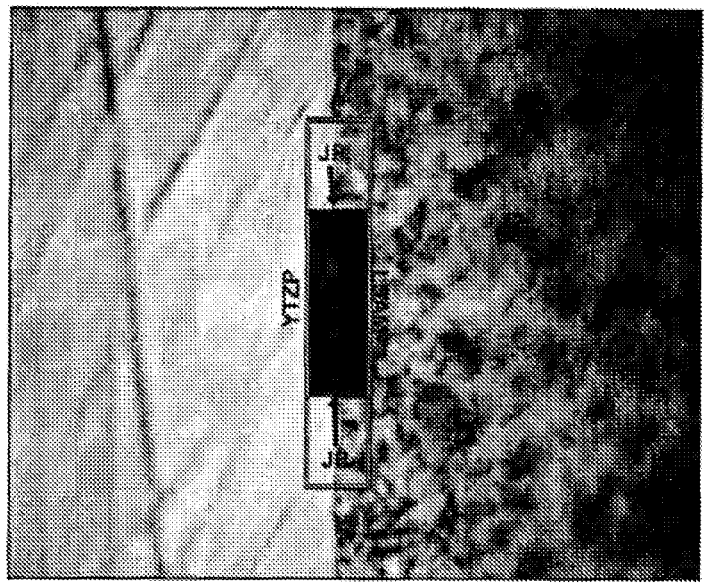
FIG. 10A illustrates a Raman image of YTZP/LSAM joined at 1350° C.
Figure 10B:
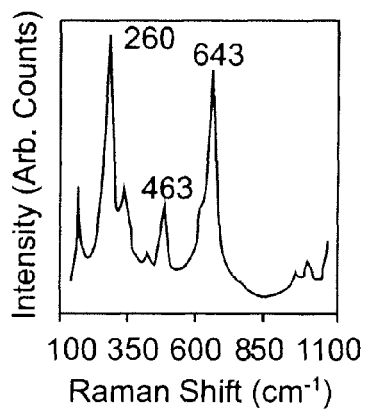
FIG. 10B shows a representative Raman spectrum of the YTZP region of FIG. 10A.
Figure 10C:
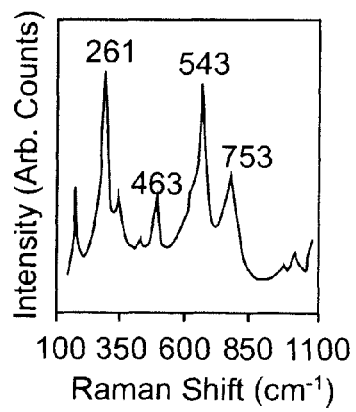
FIG. 10C shows a representative spectrum of the joining plane in FIG. 10A shown by arrows "JP"
Figure 10D:
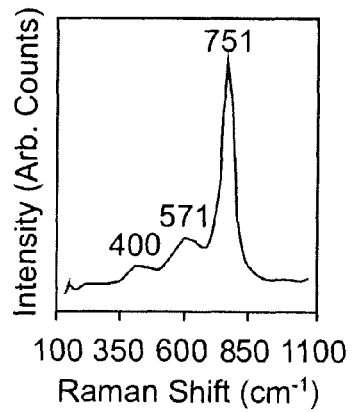
FIG. 10D shows a representative Raman spectrum of the LSAM region of FIG. 10A.

In samples joined at both 1250° C. and 1350° C., Raman peaks obtained from the YTZP bulk match that of unjoined YTZP and are shown at the left side of the scanned areas in FIGS. 9A and 10A. Raman peaks from the LSAM bulk that match that of unjoined LSAM are highlighted on the right side of the scanned area in FIGS. 9A and 10A. However, there are regions of poor matching of the spectra with a standard in the LSAM bulk (darker spots amidst the LSAM bulk in FIGS. 9A and 10A) induced by a change in intensity of the 567 cm$^{-1}$ band. As shown by the difference in FIG. 8A, curve A and curve B, the change in intensity of this band is attributed to a lower strain upon the crystallites within pores as opposed to the densified crystallites of the bulk. Strain inhomogeneity within a sample has been analyzed in the past with Raman microscopy for SiC and an intensity increase is noted in regions of comparatively lower strain. It is important to note that regions of poor agreement with the standard were diminished for the sample joined at 1350° C. as the higher temperature likely eliminated some of the porosity present before joining. Other than this change in relative intensity, samples joined at both 1250° and 1350° C. exhibited no new peaks in the bulk of either YTZP or LSAM, thereby indicating phase stability.

The joining planes marked as B in FIGS. 9A and 10A track the transition between phases and exhibit a combination of the Raman bands for LSAM and YTZP. As the laser focus is 1 μm in width and moved along the joining plane in 0.5 μm increments it is possible to identify new compounds at the interface by changes in spectral features. Based on the sharp Raman spectral transition between phases in FIGS. 9A and 10A, and the absence of any new Raman bands, we conclude no La$_2$Zr$_2$O$_7$ (LZ) or other phases are present in the joining plane (although again not limiting the scope of the claimed invention).

There are other applications of a conducting ceramic for this invention as current leads, including fuel cells (eliminating the use of the metallic interconnects), membranes for proton conduction, and β" alumina Na-ion conductor.

The following non-limiting examples illustrate various aspects of the preparation of LSAM and joining of LSAM to YTZP, and establishing stable seals to the system 10.

Example I

LSAM was synthesized via the solid-state method from the nitrates of La, Sr, Al, and the chloride of Mn by heating for 4 hours at 1000° C., grinding the product, then heating the ground mixture for fifty hours at 1200° C. The weight percentages of La, Sr, Al, and Mn determined by conventional ICP-OES were 54.1, 7.98, 2.48, and 11.48%, respectively. These weight percentages correspond to a polymorph of the formula La$_{0.77}$Sr$_{0.02}$Al$_{0.9}$Mn$_{0.1}$O$_3$. The molecular weight of this compound is 202.067 g/mol. A two-point resistivity measurement was performed of the densified wafer at 1000° C. and yielded a resistivity of 0.15 Ω·cm.

Figure 4:
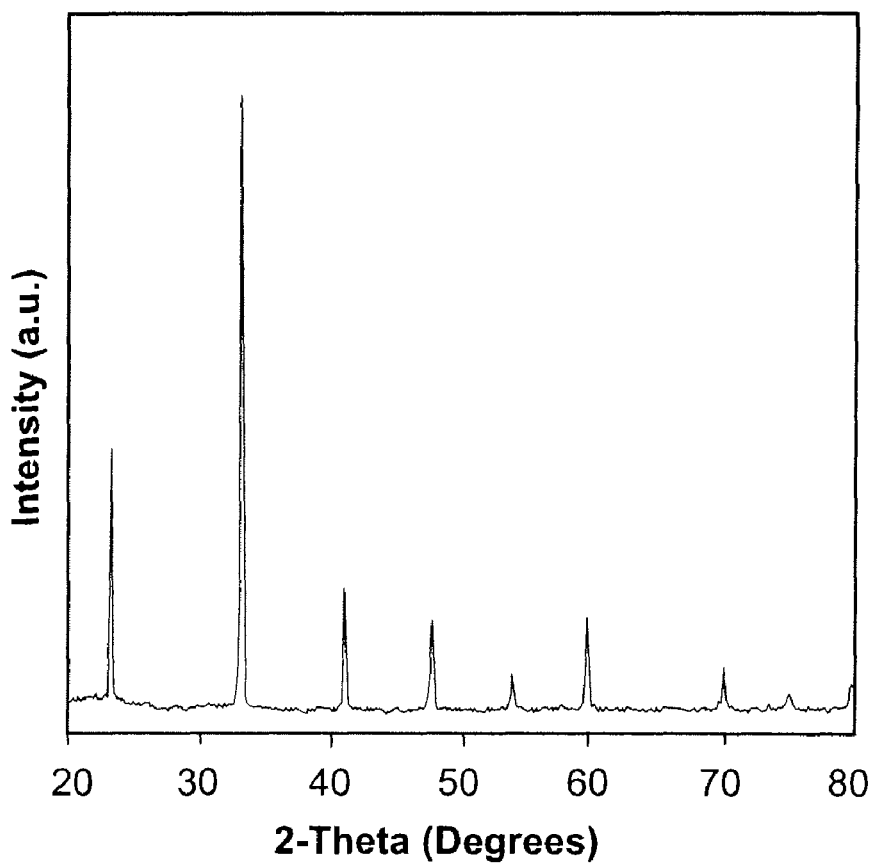
FIG. 4 illustrates an X-ray diffraction pattern of LSAM densified at 1500° C.

The powder diffraction pattern of La$_{0.77}$Sr$_{0.20}$Al$_{0.9}$Mn$_{0.1}$O$_3$ is presented in FIG. 4. No impurities or secondary phases were detected. The six peaks between 20-80° of 2θ observed were 23.36°, 33.28°, 41.12°, 47.83°, 53.93°, 59.57°, 70.03°, 75.09°, and 79.89°. The peak positions and intensities indicate that the solid state synthesis produced a material adopting a perovskite structure. This was expected based on the results of previous work which noted that partial substitution of Al for Mn with the general La$_{0.8}$Sr$_{0.2}$Al$_x$Mn$_{1-x}$O$_3$ formula will produce a single phase perovskite material. The prior art ternary phase diagram in the LaMnO$_{3+δ}$, SrMnO$_{3-δ}$, LaAlO$_3$ system indicates the possible presence of SrAl$_2$O$_4$, LaMn$_{1-x}$Al$_x$O$_3$, and La$_{1-y}$Sr$_y$MnO$_3$. However, no ternary or quaternary oxides other than LSAM are detected in the diffraction pattern.

A Pawley fit was performed on the diffraction pattern in FIG. 4 in order to determine the lattice parameters. Cubic space group Fm3m (#225) was selected for the fit as there was no peak splitting to indicate a low-symmetry cubic cell. The calculated lattice parameter of the cubic cell was 3.79627 Å with an R$_{wp}$ of 3.3. This estimate of cell volume was used to calculate the theoretical density of densified LSAM as 6.1 g/cm$^3$. The density of a sintered pellet was measured by Archimedes method as 5.6 g/cm$^3$, indicating that pellets densified for 50 hours at 1500° C. were ~92% dense. Following densification the average grain size of LSAM was estimated by SEM as ~2 μm.

Example II

Figure 3:
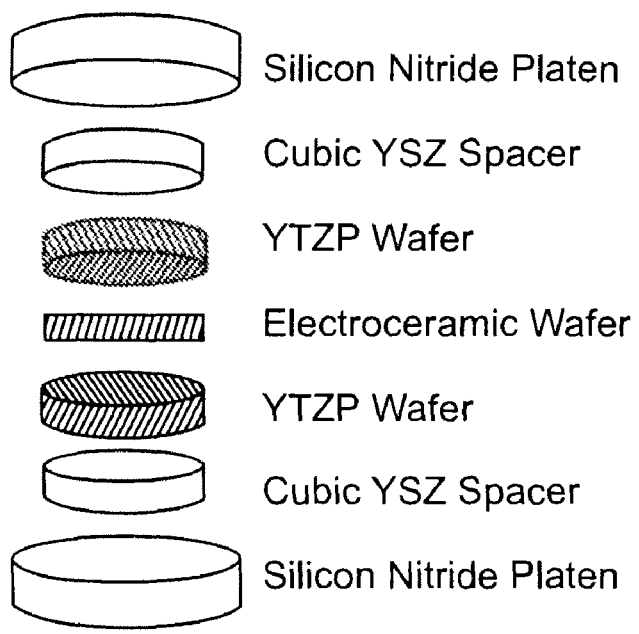
FIG. 3 illustrates a yttria stabilized tetragonal zirconia (YTZP)/LSAM joint fabrication assembly.

Each sample to be joined was constructed from the following materials and placed into a high-temperature furnace attached to a conventional Instron Universal Testing Machine (Instron, Model 1125) with silicon nitride platen (see schematic of unassembled or unjoined materials in FIG. 3). The YTZP wafers were cut from preformed and densified rods/tubes of 3 mol % yttria-stabilized tetragonal zirconia polycrystals (YTZP, average particle size ~0.4 μm) that were purchased from Custom Technical Ceramics, Inc. (Arvada, Colo.). The 8 mol % cubic yttria-stabilized zirconia spacers (YSZ, average particle size ~8 μm) were cut from a rod that was also purchased from Custom Technical Ceramics, Inc.

In order to accomplish joining, a pellet of LSAM was deformed at a strain rate ($\dot{\epsilon}$) of $4.5 \times 10^{-5}$/sec to determine the yield stress of the perovskite at 1250° C. After the yield stress of the LSAM was determined, YTZP/LSAM sandwiches were compressed in a static argon atmosphere at either 1250 or 1350° C. at crosshead speeds ranging from 0.01 mm/min to 0.02 mm/min resulting in strain rates of $4.5 \times 10^{-5}$ s$^{-1}$. During the heating cycle, the load on the sample was controlled as not to exceed 5 N. Upon reaching the target temperature, the system was left under a 5 N load for 30 min to attain thermal equilibrium. Cubic YSZ spacers and $Si_3N_4$ platens were removed following joining of YTZP to the LSAM wafer.

The foregoing description of embodiments of the present invention have been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments, and with various modifications, as are suited to the particular use contemplated.

What is claimed is:

1. A high temperature potentiometric industrial sensor comprising:
    a first platinum electrode coupled to a top surface of a first yttria stabilized tetragonal zirconia (YTZP) electrolyte wafer;
    a second platinum electrode having a distal side externally disposed relative to a sealed chamber and a proximal side internally disposed relative to the sealed chamber;
    said sealed chamber comprising: a housing having a seal layer enclosing an internal reference material within the sealed chamber and forming a single chamber containing the internal reference material, the housing including said first platinum electrode disposed on the distal side to a bottom surface of said first yttria stabilized tetragonal zirconia (YTZP) electrolyte wafer, a cylindrical ring-like $La_xSr_yAl_zMn_{1-z}O_3$ (LSAM) electronically conductive electrode layer whose stoichiometry ranges from $x+y \leqq 1$ and $0.3 \leqq z \leqq 0.9$ and is further coupled to the second platinum electrode wherein said second platinum electrode spans a gap of the cylindrical ring-like LSAM electrode layer, a second yttria stabilized tetragonal zirconia (YTZP) solid, cylindrical ring-like component coupled to the LSAM electrode layer and a third YTZP base layer coupled to said second YTZP cylindrical ring-like layer by a bond layer.

2. The high temperature potentiometric industrial sensor as defined in claim 1 wherein the ring-like LSAM conductive electrode layer consists essentially of a single phase of La, Sr, Al, Mn and O.

3. The high temperature potentiometric industrial sensor as defined in claim 1 wherein the ring-like LSAM conductive electrode layer consists of La, Sr, Al, Mn and O without any Zr.

4. The high temperature potentiometric industrial sensor as defined in claim 1 wherein the internal reference material consists essentially of a metal and metal oxide.

5. The high temperature potentiometric industrial sensor as defined in claim 1 wherein the ring-like LSAM conductive electrode layer and the second YTZP solid, cylindrical ring-like layer have substantially similar deformation characteristics and thermal expansion coefficients.

6. The high temperature potentiometric industrial sensor as defined in claim 1 wherein the seal layer is between about one micrometer and three millimeters in width.

7. The ceramic system interconnect as defined in claim 1 wherein the seal layer comprises a mechanical mixture of the LSAM electrode layer and material of the housing layer.

8. The high temperature potentiometric industrial sensor as defined in claim 1 further including a system for analyzing a signal received from the oxygen sensor for use in control of operating conditions of the industrial environment.

* * * * *